(12) United States Patent
Stergis et al.

(10) Patent No.: US 8,263,582 B2
(45) Date of Patent: Sep. 11, 2012

(54) METHOD OF TREATING INFLAMMATORY DISORDERS OF THE GASTROINTESTINAL TRACT USING TOPICAL ACTIVE CORTICOSTEROIDS

(75) Inventors: Nicholas Stergis, Miami, FL (US); George B. McDonald, Bellevue, WA (US)

(73) Assignee: Soligenix, Inc., Princeton, NJ (US)

( * ) Notice: Subject to any disclaimer, the term of this patent is extended or adjusted under 35 U.S.C. 154(b) by 0 days.

(21) Appl. No.: 10/098,968

(22) Filed: Mar. 15, 2002

(65) Prior Publication Data

US 2003/0055028 A1    Mar. 20, 2003

Related U.S. Application Data

(60) Provisional application No. 60/276,013, filed on Mar. 15, 2001.

(51) Int. Cl.
*A61K 31/573*    (2006.01)
*A61K 31/56*    (2006.01)
*A61K 31/59*    (2006.01)

(52) U.S. Cl. .................... 514/179; 514/167; 514/169

(58) Field of Classification Search ............... 514/167, 514/169, 179
See application file for complete search history.

(56) References Cited

U.S. PATENT DOCUMENTS

| 6,540,993 B1 * | 4/2003 | Warne et al. ............. 424/85.2 |
| 6,632,451 B2 * | 10/2003 | Penhasi et al. .............. 424/464 |
| 2003/0007968 A1 * | 1/2003 | Larsen et al. ............. 424/144.1 |

FOREIGN PATENT DOCUMENTS

WO   WO 00/06132   *   2/2000

OTHER PUBLICATIONS

Baehr et al. Oral beclomethaone dipropionate for treatment of human intestinal graft-versus-host disease. Transplantation, vol. 60, pp. 1231-1238, No. 11, Dec. 15, 1995.*

* cited by examiner

*Primary Examiner* — Jennifer M Kim
(74) *Attorney, Agent, or Firm* — Lewis Kohn & Fitzwilliam LLP; David M. Kohn; Kari A. Moyer-Henry

(57) ABSTRACT

A method of administration of an oral pharmaceutical product to patients suffering from inflammatory disorders of the gastrointestinal tract comprises orally administering to the patient at least two different dosage forms of a therapeutically effective amount of a topically active corticosteroid, such as beclomethasone dipropionate (BDP).

19 Claims, 2 Drawing Sheets

METHOD OF TREATING INFLAMMATORY DISORDERS OF THE GASTROINTESTINAL TRACT USING TOPICAL ACTIVE CORTICOSTEROIDS

This application claims the benefit of U.S. provisional patent application Ser. No. 60/276,013, filed Mar. 15, 2001, the entirety of which is hereby incorporated by reference.

FIELD OF THE INVENTION

This invention relates to methods for the treatment of inflammatory disorders of the gastrointestinal tract and/or bowel of a patient in need of such treatment.

BACKGROUND OF THE INVENTION

Inflammatory bowel disease (IBD) is a general term that refers to conditions characterized by chronic inflammation of the tissues that comprise the digestive tract. Symptoms associated with IBDs may include abdominal pain and cramps, diarrhea, weight loss and intestinal or rectal bleeding. Up to one million Americans suffer from either of these two diseases, with roughly equal numbers for each. The causes of these diseases are unknown.

The two most common forms of IBD are ulcerative colitis and Crohn's disease. Less common forms of IBD include collagenous and lymphocytic colitis and colitis associated with enteric microbial pathogens. Ulcerative colitis is an inflammatory disorder of the large bowel (colon and rectum) characterized by inflammation and ulceration of the innermost lining of the colon. Symptoms include abdominal pain, abdominal cramping, decreased appetite and weight loss, tenesmus, and diarrhea, which may be accompanied by rectal bleeding. Inflammation associated with ulcerative colitis can involve the entire length of the colon but is usually greatest in the rectum and may extend continuously for varying distances along the colon, occurring most typically in a proximal to distal pattern of inflammation.

Crohn's disease is another type of inflammatory bowel disease. Crohn's disease can affect any portion of the digestive tract, but is most commonly seen in the distal portion of the small intestine. Approximately 40% of Crohn's disease patients have inflammatory disease localized in the ileocecal region, 30-35% of the patients have disease in the proximal small bowel and the stomach, and about 25% of patients have disease localized in the large bowel. Unlike ulcerative colitis, Crohn's disease can exhibit areas of normal intestine between regions of affected intestine, termed "skip" areas. Also, Crohn's disease is distinguishable from ulcerative colitis in that ulcerative colitis affects only the innermost lining of the colon, while in Crohn's disease the entire thickness of the bowel wall is involved, often resulting in fistulae.

Treatment of IBDs usually involves administration of aminosalicylates (i.e., 5-aminosalicylic acid or sulfasalazine); immunomodulatory compounds (i.e., azathioprine, cyclosporine or 6-mercaptopurine); steroid drugs (i.e., prednisone, methylprenisolone, or budesonide); or monoclonal antibodies directed to cytokines, such as TNF-alpha, and other inflammatory mediators. Anti-TNF alpha antibodies have been used successfully to treat steroid-refractory fistulating Crohn's disease. Aminosalicylates are used to treat mild to moderate cases of IBD and are usually the first line therapy for patients initially presenting with Crohn's disease. In addition, immunomodulatory drugs such as methotrexate or azathioprine are routinely given to patients who fail to respond to aminosalicylates. However, the immunomodulatory drugs may take up to three months to begin to take effect and can also result in increased risk of neoplastic diseases. In severe cases, surgery to remove the affected areas of the colon or bowel may be required. Surgery is inevitably required to treat chronic Crohn's disease of decades duration.

The treatment of choice for moderate to severe ulcerative colitis and Crohn's disease is administration of steroid drugs, which are potent anti-inflammatory agents. Steroid drugs may be administered orally, intravenously, via an enema or via a suppository, depending on the location, severity and extent of the disease. In most instances, steroid drugs are given orally and occasionally parenterally. Steroids are typically given to ablate the initial symptoms of inflammation and are rarely given repetitively over long term because of the side effects. Oral administration is most preferred for its ease and effectiveness. The steroid drugs used routinely in treating IBD are prednisone, methylprednisone or prednisolone. However, the use of such steroids by oral, topical or injection routes of administration results in high levels of the steroid drug in the systemic circulation. Long term used of these drugs beyond daily doses over a period of several weeks can result in a variety of undesirable side effects, including weight gain, thinning of the epidermis, moon face, acne, facial hair, hypertension, mood swings, and increased susceptibility to infection, and diminishment of the hypothalamic-pituitary-adrenal (HPA) axis.

Steroid drugs may retain potent activity when administered topically, a characteristic which has been successfully utilized in the treatment of asthma and certain skin disorders. However, since systemic absorption of steroid drugs occurs even when the drugs are administered topically, the same undesirable side effects are produced. Therefore, there remains a need for a method to treat IBDs, such as ulcerative colitis and Crohn's disease, that can take advantage of the powerful anti-inflammatory properties of steroid drugs without producing the associated undesirable side effects.

Steroids with topical, but moderate systemic activity have been characterized and have been used in the treatment of IBD. A variety of steroid analogues has been developed over the last several decades. These steroids characteristically have high activity in vitro in binding to steroid receptors, but in vivo are rapidly metabolized in the liver to inactive or less active metabolites. High degree of first pass metabolism in the liver largely bypasses the undesirable toxic side effects of steroid administration. To be effective in treatment of IBD, a topically active steroid must be formulated in such a manner to reach the affected inflamed portions of the gastrointestinal tract. This has been accomplished by producing galenic formulations of topical steroids that can be administered as enemas to treat ulcerative colitis or controlled release formulations that can be taken orally to treat inflammation in the small or large intestine. Controlled release formulations are typically designed to release drug conditionally from a polymer matrix, for instance, when encountering a change in pH of the milieu, or by simple erosion of the matrix and diffusion of the drug from the matrix. For example, U.S. Pat. No. 5,643,602 describes formulation of budesonide and other steroids analogues coating a core consisting of a non-pareil seed and where the core is further surrounded by a polymeric coating that dissolved at high pH found in the ileocecal region of the intestine. The formulations described in U.S. Pat. No. 5,643,602 are thus designed to release topical steroid slowly in the small intestine and consequently little topical drug is available in the proximal segment of the small intestine. U.S. Pat. No. 6,096,731 further discloses prophylaxis of liver and cellular damage arising from graft versus host disease using beclomethasone formulated in gelcapsules and enteric coated gel capsules. Therefore, what is needed in the treatment of Crohn's disease is formulations of topical steroids that effectively treat both proximal and small bowel inflammation and inflammation in the stomach. Additionally, what is need is a formulation of a topical steroid that will reach sufficient local concentration in the distal small bowel and the colon for treatment of colitis.

SUMMARY OF THE INVENTION

A method of administration of an oral pharmaceutical product to patients suffering from inflammatory disorders of the gastrointestinal tract comprises orally administering to the patient at least two different dosage forms of a therapeutically effective amount of a topically active corticosteroid or a pharmaceutically active salt thereof, such as beclomethasone dipropionate.

Accordingly, it is an object of the present invention to provide a method of treating an inflammatory bowel disease, comprising administering to a patient in need of such treatment at least two separate dosage forms of a topically active corticosteroid or a pharmaceutically active salt thereof; the dosage forms containing an amount of the topically active corticosteroid that is sufficient to reduce or eliminate symptoms associated with the inflammatory bowel disease and sufficient to reduce or eliminate side effects associated with systemic levels of steroid drug administration.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE INVENTION

Figure 1:
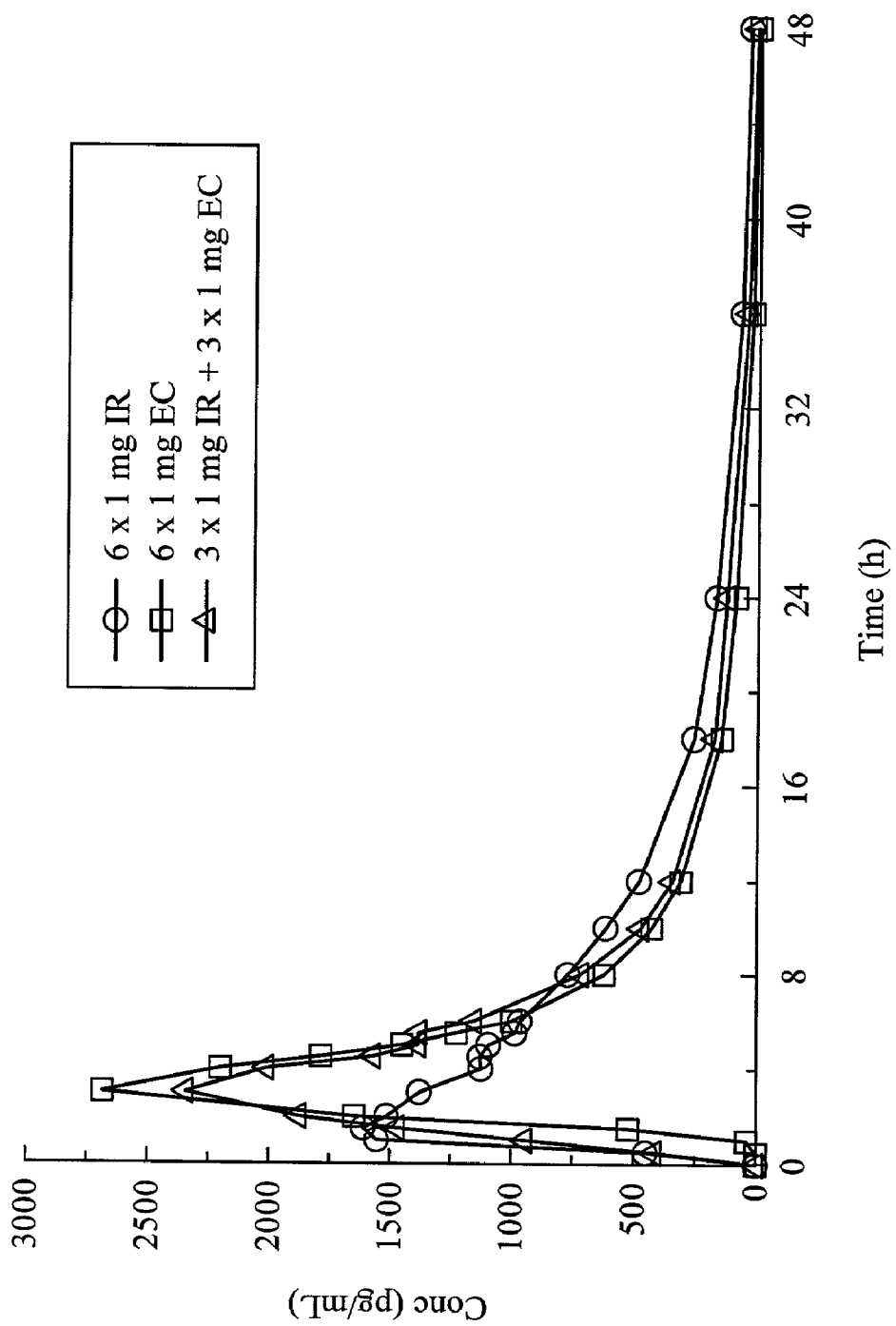
FIG. 1 illustrates mean plasma concentrations of 17-BMP after oral administration of 6 mg of BDP as IR, EC, or a Combination of IR and EC Tablets under fasted conditions to healthy volunteers.

The present invention provides methods for treating IBDs that comprises oral administration of a topically active corticosteroid, or a pharmaceutically acceptable salt thereof, in a dosage which is therapeutically effective for topical treatment of an IBD, but which does not permit development of levels of the drug in the systemic circulation sufficient to produce the side effects usually found with steroid drugs. A therapeutically effective dose of the selected topically active corticosteroid drug is introduced into the gastrointestinal tract as an oral agent and that portion of the dose that crosses the wall and enters the circulation is effectively metabolized and inactivated before reaching the systemic circulation. Alternatively, the topically active corticosteroid may be one that does not readily cross the intestinal or stomach wall. The side effects are therefore substantially reduced.

As used herein, the term "topically active" refers to a drug that has a high topical activity on the gastrointestinal mucosa at a low dosage, or, alternatively, one that has a high topical activity and which does not readily cross the gastrointestinal tract wall. The term "therapeutically effective dosage" refers to an amount of the drug that is sufficient to reduce or eliminate symptoms of an IBD in a patient. The term "systemic circulation" refers to that portion of the circulation which is distal to the site of steroid drug metabolism, in which a steady-state level of the drug in the circulation has been achieved. The present invention has been primarily developed for use in the treatment of inflammatory bowel disorders of the gastrointestinal tract, e.g. ulcerative colitis, proctitis, sigmoiditis, pan-colitis, and Crohn's Disease, although it is not limited to the treatment of the recited conditions and may be used in treatment of other conditions that exhibit inflammation of the gastrointestinal tract. The term "pharmaceutically acceptable salt" refers to derivatives of the free acid or base forms of the disclosed compounds that are modified by addition of appropriate salts. Examples include mineral or organic acid salts of basic residues, such as amines, and alkali or organic salts of acidic residues, such as carboxylic acids.

In one embodiment of the invention, the topically active corticosteroid is administered in at least two separate dosage forms, including at least one each of an immediate release and an enteric coated composition. An "immediate release" formulation is one that is intended and formulated to dissolve and have activity in the in the initial portions of the gastrointestinal tract, such as the stomach, the duodenum and the proximal small bowel. An "enteric coated" formulation is one that is intended and formulated to dissolve and have activity in the lower intestinal tract, such as the distal small intestine, the ileocecal region or colon (large intestine). The two separate dosage forms may contain equal or different amounts of the topically active corticosteroid. While the present invention is not intended to be limited to this embodiment, the embodiment in which the topically active corticosteroid in two different dosage forms encompasses the basic and novel characteristics of the invention.

The two separate dosage forms may also contain another drug, such as other corticosteroids, a non-steroidal anti-inflammatory drug, an immunosuppressive agent or an antibiotic. Examples of such steroid drugs are prednisone, prednisolone, triamcinolone, alclometasone, desoximetasone, and betamethasone. Examples of non-steroidal anti-inflammatory drugs include, for example, aspirin, ibuprofen, naproxen, indomethacin, diclofenac, sulindac, piroxicam, etodolac, ketoprofen, and tolmetin. Examples of immunosuppressive agents include, for example, cyclosporin A and analogs thereof, FK506 and analogs thereof, azathioprine, mycophenilic acid, rapamycin, methotrexate, and tacrolimus. Examples of antibiotics include penicillin, erythromycin, ampicillin, ciprofloxacin, vancomycin, stretomycin, polymyxin, tetracycline and their derivatives.

The preferred topically active corticosteroid drugs suitable for use in the methods of the present invention are beclomethasone dipropionate (BDP) and betamethasone-17-valerate, due to their high topical activity and effectiveness at low dosages. The most preferred drug is beclomethasone 17,21-dipropionate, due to its high topical anti-inflammatory activity. However, the invention is not restricted thereto, and is intended to encompass any steroid drug which is substantially topically active. Other such steroid drugs include, for example, alclometasone dipropionate, busedonide, 22S busesonide, 22R budesonide, beclomethasone-17-monopropionate, clobetasol propionate, diflorasone diacetate, flunisolide, flurandrenolide, fluticasone propionate, halobetasol propionate, halcinocide, mometasone furoate, and triamcinalone acetonide. The preferred dosage level of the topically active corticosteroid will generally range from 0.1 mg/day to 8 mg/day, and more typically range from 2 mg/day to 4 mg/day. More preferably, the dosage is not more than about 2 mg, preferably not more than about 1 mg, administered at a time, e.g. daily. The dosage level should be such that the drug does not enter the systemic circulation to any significant extent, i.e., in amounts high enough to cause adverse systemic effects, and hence these effects resulting from their presence in the systemic circulation are avoided. Alternatively, the dosage level should be such that the amounts that cross the wall of the gastrointestinal tract are less than that required to induce the undesirable side effects associated with such drugs.

It is preferable to limit the number of separate dosage forms to the smallest number possible; thus, two separate dosage forms is the preferred embodiment. In general terms, when delivered using two different dosage forms, the patient receives the topically active corticosteroid throughout the entire gastrointestinal tract, from the stomach to the rectum. For example, one dosage form may be formulated as a gelcapsule, and the second dosage form may be formulated as an enteric coated gelcapsule.

In one embodiment of the invention, the separate dosage forms are administered to a patient as separate tablets, pills, troches, gelcaps and the like. In this embodiment, the separate dosage forms are designed to contain a first dosage form containing a topical corticosteroid that releases in the stomach and a second dosage form containing a topical corticosteroid that releases in the intestine, such that the simultaneous administration of the two dosage forms results in a combination of quick release and slow release of the topical corticosteroid. In yet another preferred embodiment of the invention, the separate dosage forms are combined in a single formulation form, i.e., a tablet or a single gelcap, for oral administration to a patient. In this embodiment of the invention, the topical corticosteroid may be formulated in microspheres, polymer microspheres, hydrogels, water-in-oil emulsions, oil-in-water emulsions, liposomes, micelles, or reverse micelles to control the release of the topical steroid in the small intestine, and separately the topical corticosteroid is added external to the microspheres or drug delivery vehicle in a suitable matrix to allow for rapid release of the topical corticosteroid. In other words, such a formulation would contain an inner core containing, for example, an enteric coated formulation of the topical corticosteroid, and an outer shell surrounding the core and containing a rapid release formulation of the drug. Note also that one or the other of the inner core or outer shell could optionally contain a second drug different from the topical corticosteroid. Such a combination results in a single formulation with both slow release and quick release characteristics. Suitable polymeric systems for entrapment of topical steroids in microspheres, hydrogels, and nanospheres include, but are not limited to, single component polymer systems and combinations of polyalkylene oxide homopolymers, polyethylene glycol, polypropylene glycols, polyoxyethylenated polyols, polyols, polyimines, polypeptides, polyglutamic acid, polylysine, polyaspartic acid, polyacid esters, polyacrylic acid, alginate, hyaluronic acid, chitosan, carboxymethyl cellulose, hydroxypropylmethyl cellulose oligosaccharides, polysaccharides, carageenan and salts thereof, dextran, deacetylated chitosan, gelatin, block co-polymers, block co-polymers of polyoxyethylene and polyoxypropylene, methoxy-PEG, methoxy-PEG amine, polyacrylyl amides, polyvinyl pyrollidones, poly lactic, polyglycolic acid, polyvinyl alcohols, and co-polymers thereof.

BDP is available from a number of commercial sources, such as Schering-Plough Corporation (Kenilworth, N.J.) in bulk crystalline form. Beclomethasone 17,21-dipropionate has the following structure:

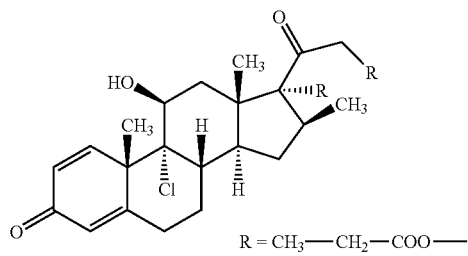

The topically active corticosteroid used in the methods of the present invention may be formulated for oral administration by techniques well known to those in the in the drug formulation field, including formulation as a capsule, pill, troche, coated microsphere with specific dissolution qualities, or emulsion. Suitable capsules or pills generally contain from 0.1 mg to 8 mg of the topically active corticosteroid, and typically about 1 mg, plus optional fillers, including but not limited to binders, such as microcrystalline cellulose, gum tragacanth or gelatin; fillers, such as starch or lactose; disintegrating agents, such as con starch or alginic acid; sweetening agents, such as sucrose, saccharin or phenylalanine; or flavoring agents, such as peppermint, lemon, cinnamon, methyl salicylate, or orange flavoring. In addition, the capsules or pills may be coated with a variety of materials, such as sugars, shellacs or cellulose acetate phthalate. By adding an appropriate coating, the capsules, microspheres or pills may be made to dissolve within various location of the intestinal tract. For example, enteric-coated capsules prepared with a coating of cellulose acetate phthalate are known to remain intact in the stomach and dissolve in the alkaline environment of the small bowel, thus delivering its content to the small bowel and colon. Other useful enteric coatings may include hydroxypropyl methylcellulose phthalate, polyvinyl acetate phthalate, and those polymers based on methacrylic acid-methacrylic acid ester co-polymers with acidic ionizable groups known to those in the art under the trade name "Eudragit" (Roehm GmbH & Co., Darmstadt, Germany).

The topically active corticosteroid may also be formulated as an oil-in-water emulsion, a water-in-oil emulsion, a multiple emulsion, (w/o/w), entrapped or associated with liposomes, and/or organized lipid phases. Lipid-based delivery systems such as emulsion systems, microemulsions systems, or lipid particulate systems are based on the use of polar lipids and related amphiphilic surfactant molecules to control the interaction of hydrophobic molecules with water. In many cases, delivery systems for hydrophobic drugs have also required the inclusion of organic solvents that are water miscible in order to increase the molecular interactions between drugs and lipid or surfactant components.

Lipids and surfactants are differentiable from short and long chain hydrocarbons in that they are amphiphilic molecules, having both hydrophilic and hydrophobic moieties. Surfactants are conveniently classified on an empirical scale known as the hydrophile-lipophile balance (HLB) which runs from about 1 to about 45 and from about 1 to about 20 for non-ionic surfactants. HLB values closer to 1 represent surfactants with more lipophilic character, while HLB values that are greater than about 10 represent more hydrophilic surfactants. In contact with water, surfactants form different kinds of aggregates. Phospholipids characteristically form bilayer membranes in water, whereas at low concentration of other polar lipids in water, micellar structures form. Depending on the concentration of polar lipid in water, micelles are either spherical, typically containing 50-100 lipid molecules, or rod-shaped or disc-shaped macrostructures. In each of these cases, the hydrocarbon tails form the interior of the micelle and polar head groups are in contact with water. At higher concentration of polar lipid in water, reverse-type micelles, or inverse micelles, form. The conventional micellar phase is also known as the L1 phase. The reverse micellar phase is also known as L2. In the L2 phase, water forms the internal phase and the hydrophobic tails of the lipid form the continuous phase. Micelles, and pharmaceutical compositions containing micelles, have been extensively studied and are described in detail in the literature; see, e.g., Remington's Pharmaceutical Sciences, 17th ed. (1985). In aqueous solution, micelles can incorporate hydrophobic therapeutic agents in the hydrocarbon core of the micelle.

Oil-in-water (o/w) emulsions are also commonly formed from oil(s), surfactant(s), and an aqueous phase. Typically oils used that comprise drug delivery systems are made to solubilize lipophilic drugs to make them more effective and less toxic. Oils used in typical emulsions are any of a number of oils such as mineral, vegetable, animal, essential and synthetic oils, or mixtures thereof. In many cases oils rich in triglycerides, such as safflower oil, cottonseed oil, olive oil or soybean oil are used. In its simplest form, a triglyceride-containing formulation suitable for delivering hydrophobic therapeutic agents is an oil-in-water emulsion containing the therapeutic agent. Such emulsions contain the hydrophobic therapeutic agent such as beclomethasone diproprionate solubilized in an oil phase that is dispersed in an aqueous environment with the aid of a surfactant or a combination of surfactants. Therefore, one approach to making suitable formulations of hydrophobic topical steroid drugs is to solubilize it in an oil and to disperse this oil phase in an aqueous solution. Depending on whether an oil is a solid or liquid at the ambient temperature, the oil-in-water emulsion can be characterized as a solid lipid particulate. Surfactants are also required to form solid emulsions. And the same forces that operate in liquid oil phase also cause the precipitation of hydrophobic drugs at the interface of lipids with water upon short or long term storage and destabilize lipid particle suspension systems. The dispersion may be stabilized by emulsifying agents and provided in emulsion form. In a water milieu, drugs dissolved in the oil phase or the solid lipid core phase may be dispersed by mechanical force to create microdroplets or microspheres suspended in the aqueous phase that are stable in storage as a pharmaceutical preparation.

The formation of a stable oil-in-water emulsion may be enhanced by the use of surfactants that form the interface between the strictly hydrophobic oil and water. Depending on the nature of the oil and one or more surfactants, either large droplets characteristic of oil-in-water emulsions or much smaller structures characteristic of micellar structures are formed. Further control over size of droplets or particles can be obtained by high pressure homogenization or similar shear forces. Lipid particles are typically formed at higher ambient temperatures to melt the hydrophobic components.

Hydrophobic therapeutic agents, while poorly soluble in aqueous solution, may be sufficiently lipophilic such that therapeutically effective concentrations can be prepared in triglyceride-based solvents forming colloidal oil particles, with broad particle size distribution and relatively large sizes, ranging from several hundred nanometers to several microns in diameter. Reverse micelles containing oil(s), surfactant(s) and an aqueous phase are also characterized as water-in-oil microemulsions (see Constantinides, P.P. Lipid Microemulsions for Improving Drug Dissolution and Oral Absorption: Physical and Biopharmaceutical Aspects, *Pharm. Res.* 12 (11) 1561-1572, 1995 and references therein). In addition, a number of liquid crystalline structures can also co-exist in mixtures of polar lipid and water, analogous to normal and inverse micelles, including hexagonal phases and inverse hexagonal. Traditionally, simple reverse micelles (water/amphiphile) have not been used in mucosal drug delivery systems.

Microemulsion systems are ternary or quaternary systems typically formed from an oil phase, a surfactant, and water. For example, U.S. Pat. No. 5,707,648 describes microemulsions that contain an oil phase, an aqueous phase, and a mixture of surfactants. The solubilization of one phase into another in a microemulsion system is affected by a balance of attractive and repulsive forces. Microemulsions are thermodynamically stable, such that the droplets will not coalesce and precipitate over time. The diameter of microemulsion droplets is in the range of 10 to 200 nanometers, while emulsion droplets are generally greater than a micron. The interface of microemulsion droplets can be considered as a monolayer of surfactant. A microemulsion can be characterized by the amount of the dispersed phase solubilized in the continuous phase. Microemulsions have traditionally been formed using, in addition to the components described above, a cosurfactant, which are generally short chain alcohols, ethanol or butanol, glycols such as propylene glycol and polyethylene glycol, or medium chain alcohols, amines, or acids. In a liquid form, the emulsions or lipid formulations of beclomethasone may be suitably encapsulated in gelcaps.

One skilled in the art may further formulate the drug in any appropriate manner, and in accordance with accepted practices, such as those disclosed in Remington's Pharmaceutical Sciences, Gennaro, Ed., Mack Publishing Co., Easton, Pa., 1990 (incorporated herein by reference).

An important aspect of this invention is that the topically active corticosteroid is orally administered such that it is topically administered to the intestinal and/or liver tissue. Thus, oral administration, as that term is used herein, is intended to exclude systemic administration, such as is achieved by intravenous injection. Rather, the methods are intended to achieve administration of the topically active corticosteroid so that it has high topical activity on intestinal and/or liver tissue with little or no systemic availability. The high topical activity is achieved by any of a number of means, known to those in the art, of limiting the distribution of the drug to the intestinal mucosa. For example, the drug may be formulated so as to coat the surface of the intestinal mucosa with a high local concentration of the drug, or formulated so as to inhibit traversal of the drug across the intestinal mucosal into the systemic circulation. Such limited distribution results in fewer side effects, which is a significant advantage of this invention.

By appropriate formulation of the topically active corticosteroid (using i.e., the dual tablet formulation containing one each of an immediate release formulation and an enterically coated formulation), it can be delivered to the entire mucosal surface of the entire intestine in high doses. Thus, the topically active corticosteroid can achieve high concentrations throughout the intestinal mucosa where this initiating immune reaction is taking place.

The invention will now be further described by use of the following examples. It will be appreciated that, although specific embodiments of this invention are described herein for purpose of illustration, various modifications may be made without departing from the spirit and scope of the invention.

EXAMPLES

Example 1

Formulation of Beclomethasone Diproprionate in Immediate Release (IR) and Enteric Coated (EC) Tablets The components of the immediate release (IR) and delayed release (enteric coated (EC)) tablets used in the Examples are listed in Table 1.

TABLE 1

Composition of delayed release and immediate release beclomethasone tablets

| Component | Amount | |
|---|---|---|
| | Immediate release (mg/tablet) | Enteric-coated (mg/tablet) |
| Core tablet | | |
| Beclomethasone diproprionate | 1.0 | 1.0 |
| Lactose | 153 | 153 |
| Microcrystalline cellulose | 40.0 | 40.0 |
| Povidone | 4.0 | 4.0 |
| Magnesium stearate | 1.0 | 1.0 |
| Coating | | |
| Methacrylic acid copolymer | N/A | 11.4 |
| Triethyl citrate | N/A | 1.7 |
| Polysorbate 80 | N/A | 0.025 |
| Silicon dioxide | N/A | 0.91 |
| Sodium hydroxide | N/A | 0.03 |

N/A = not applicable

Example 2

Treatment of Volunteers with Immediate Release and Delayed Release Tablets of Beclomethasone 12 healthy adult volunteers received a single 6 mg dose of BDP as one of four combinations of IR and EC tablets. Blood samples were drawn at a number of specified time points to determine plasma BDP, beclomethasone-17-monopropionate (17-BMP), and beclomethasone (BOH) concentrations to assess the bioavailability of the two tablet formulations. After a 5-day washout period, the same subjects received a single oral dose of the next combination. This was repeated until each subject had received all treatments. At the 0 hour of Days 1, 8, 15, and 22, subjects received one of the following treatments:
  A: 6×1 mg BDP IR tablets administered under fasting conditions;
  B: 6×1 mg BDP EC tablets administered under fasting conditions;
  C: 3×1 mg BDP IR tablets+3×1 mg BDP EC tablets administered under fasting conditions.

All doses were administered with 180 mL of water. Blood samples (7 mL) were collected before and 0.5, 1, 1.5, 2, 3, 4, 4.5, 5, 5.5, 6, 8, 10, 12, 18, 24, 36, and 48 hours after each dose. Blood samples were stored on ice until processing and storage. Plasma samples were separated by centrifugation and then frozen at $\leq 20°$ C. until assayed. Plasma samples were analyzed for BDP, 17-BMP, and BOH concentrations using validated liquid chromatography/mass spectrometry/mass spectrometry (LC/MS/MS) methods.

Example 3

Pharmacokinetics of Immediate Release and Delayed Release Beclomethasone Tablets Pharmacokinetic parameters for BDP, 17-BMP, and BOH in plasma were calculated using non-compartmental analysis. Only those plasma concentrations equal to or greater than the validated lower limits of the assays (LOQ) were used in the analysis. The LOQs for BDP, 17-BMP, and BOH were 5 pg/mL, 20 pg/mL, and 20 pg/mL, respectively. The maximum plasma concentration ($C_{max}$) and time to $C_{max}$ ($T_{max}$) were taken directly from the data. The absorption lag time ($T_{lag}$) was estimated as first time after drug administration for which the plasma concentration was $\geq$LOQ and was taken directly from the data. The elimination rate constant, $\lambda_z$, was calculated as the negative of the slope of the terminal log-linear segment of the plasma concentration-time curve. Elimination half-life ($t_{1/2}$) was calculated according to the following equation.

$$t_{1/2} = \frac{0.693}{\lambda_z}$$

Area under the curve from zero to the final sample with a concentration $\geq$LOQ ($AUC_{0-t}$) was calculated using the linear trapezoidal method and extrapolated to infinity using $$AUC_\infty = AUC_{0-t} + \frac{C_{tf}}{\lambda_z}$$

where $C_{tf}$ is the final concentration $\geq$LOQ. All pharmacokinetic calculations and statistical analyses were done using SAS® for Windows® Version 8.

Figure 2:
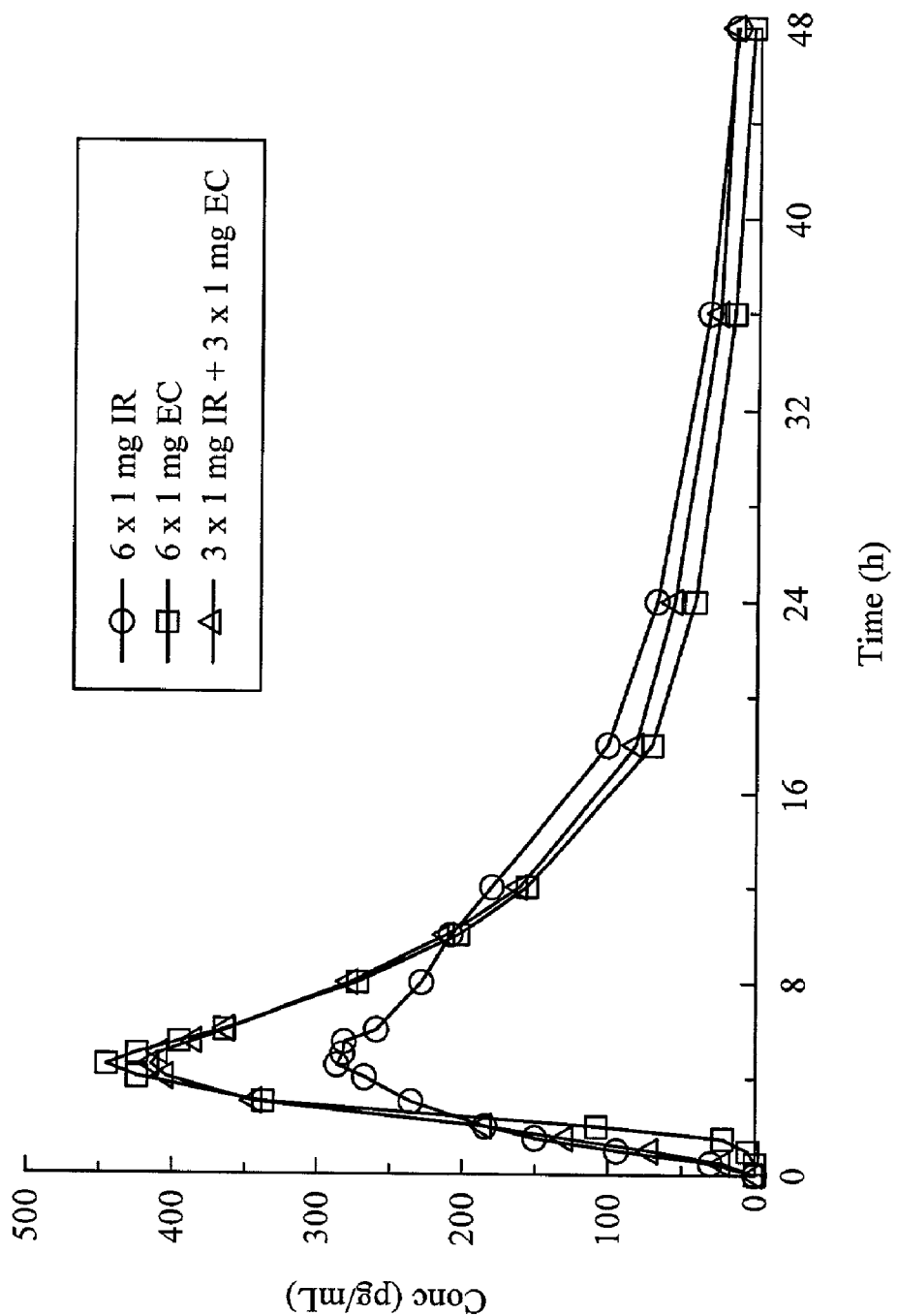
FIG. 2 shows mean plasma concentrations of BOH after oral administration of 6 mg of BDP as IR, EC, or a combination of IR and EC Tablets under fasted conditions to healthy volunteers.

There were no BDP plasma concentrations $\geq$LOQ (5 pg/mL) for any subject for any of the treatments. As a consequence of the time required for transfer from the stomach into the intestine, the absorption lag times for both 17-BMP and BOH after administration of the EC tablets were longer than those for the IR tablets (Table 2). The "lag time" for the IR tablets was the same as the first sampling time (0.5 h), implying no measurable delay in absorption from that formulation. Plasma 17-BMP (FIG. 1) and BOH (FIG. 2) concentrations after administration of the EC tablet were higher than those from the IR tablet. Concurrent administration of the IR and EC tablets resulted in plasma concentrations of both 17-BMP (FIG. 1) and BOH (FIG. 2) similar to those of the EC tablet alone but with no lag time. $C_{max}$ of both were essentially the same while mean values for $AUC_\infty$ were 10% to 20% higher for the combination as compared to the EC tablet alone (Table 2).

TABLE 2

17-BMP and BOH Pharmacokinetic Parameters after Oral Administration of 6 mg of BDP as IR, EC, or a Combination of IR and EC Tablets under Fasted Conditions to Healthy Volunteers

| | Treatment | | |
|---|---|---|---|
| Parameter[1] | 6 × 1 mg IR | 6 × 1 mg EC | 3 × 1 mg IR + 3 × 1 mg EC |
| 17-BMP | | | |
| $T_{lag}$ (h) | 0.50 | 1.50 | 0.50 |
| $C_{max}$ (pg/mL) | 2,049 ± 1,251 | 3,026 ± 1,594 | 2,929 ± 1,088 |
| $T_{max}$ (h) | 3.52 | 3.00 | 3.00 |
| $AUC_{0-t}$ (h · pg/mL) | 15,543 ± 4,914 | 13,663 ± 5,215 | 16,040 ± 5,306 |
| $AUC_{\infty}$ (h · pg/mL) | 17,130 ± 5,848 | 14,781 ± 5,294 | 16,677 ± 5,544 |
| $t_{1/2}$ (h) | 10.9 ± 8.04 | 6.07 ± 2.32 | 8.86 ± 3.72 |
| BOH | | | |
| $T_{lag}$ (h) | 1.00 | 2.00 | 1.00 |
| $C_{max}$ (pg/mL) | 346 ± 168 | 476 ± 190 | 466 ± 138 |
| $T_{max}$ (h) | 4.50 | 4.50 | 4.50 |
| $AUC_{0-t}$ (h · pg/mL) | 4,501 ± 1,811 | 4,074 ± 1,461 | 4,598 ± 1,867 |
| $AUC_{\infty}$ (h · pg/mL) | 5,373 ± 2,247 | 4,635 ± 1,451 | 4,661 ± 1,514 |
| $t_{1/2}$ (h) | 11.2 ± 8.35 | 5.54 ± 2.13 | 7.21 ± 3.53 |

[1]Mean ± standard deviation except for $T_{lag}$ and $T_{max}$ for which the median is reported.

Based on the plasma concentrations of 17-BMP and BOH, the IR and EC BDP tablet formulations release BDP after oral administration, with approximately 20% greater bioavailability from the latter. Concurrent administration of IR and EC tablets resulted in plasma concentrations similar to those of the EC alone.

We claim:

1. A method of treating an inflammatory bowel disease selected from the group consisting of ulcerative colitis, proctitis, sigmoiditis, pan-colitis and Crohn's disease, comprising administering to a patient at least two separate oral dosage forms of beclomethasone dipropionate or a pharmaceutically active salt thereof; said dosage forms containing an amount of beclomethasone dipropionate or a pharmaceutically active salt thereof that is sufficient to reduce or eliminate symptoms associated with said inflammatory bowel disease and sufficient to reduce or eliminate side effects associated with systemic levels of steroid drug administration, and wherein one dose is formulated to release in the stomach and one dose is formulated to release in the small intestine or colon, and further wherein the said two different dosage forms are combined into a single delivery device for oral administration.

2. The method of claim 1 wherein said at least two oral dosage forms contain different amounts of beclomethasone dipropionate.

3. The method of claim 1 wherein said at least two oral dosage forms contain equal amounts of beclomethasone dipropionate.

4. The method of claim 1, wherein beclomethasone dipropionate is administered at a dosage of 0.1 mg per day to 8 mg per day.

5. The method of claim 1, wherein beclomethasone dipropionate is administered at a dosage of 2 mg per day to 4 mg per day.

6. The method of claim 1, wherein beclomethasone dipropionate is administered in combination with prednisone and prednisolone.

7. The method of claim 1, wherein said dose formulated to release in the small intestine or colon is an enterically coated dosage form.

8. The method of claim 1, wherein at least one of said oral dosage forms is formulated as an emulsion.

9. The method of claim 1, wherein said single formulation form further contains an immunosuppressant.

10. The method of claim 1, wherein said single formulation form further contains cyclosporine A.

11. The method of claim 1, wherein said single formulation form further contains methotrexate.

12. The method of claim 1, wherein said single formulation form further contains azathioprine.

13. A method of treating an inflammatory bowel disease selected from the group consisting of ulcerative colitis, proctitis, sigmoiditis, pan-colitis and Crohn's disease comprising the following steps:
  (a) providing a formulation of a topically active corticosteroid, wherein the formulation is engineered to deliver at least one dose of the topically active corticosteroid to the stomach and at least one dose to the small intestine or colon; and
  (b) orally administering the formulation to a patient, wherein the formulation has topical activity on the patient's gastrointestinal mucosa and further wherein the topically active corticosteroid is beclomethasone dipropionate.

14. The method of claim 13, wherein the formulation contains different amounts of beclomethasone dipropionate.

15. The method of claim 13, wherein the formulation contains equal amounts of beclomethasone dipropionate.

16. The method of claim 13, wherein the formulation is administered at a dosage of 0.1 mg per day to 8 mg per day.

17. The method of claim 13, wherein the formulation is administered at a dosage of 2 mg per day to 4 mg per day.

18. The method of claim 13, wherein the formulation is administered in combination with prednisone and prednisolone.

19. The method of claim 13, wherein at least one of the oral dosage forms is formulated in the form of a tablet, pill, capsule or microsphere.

* * * * *

UNITED STATES PATENT AND TRADEMARK OFFICE
CERTIFICATE OF CORRECTION

| | | |
|---|---|---|
| PATENT NO. | : 8,263,582 B2 | Page 1 of 1 |
| APPLICATION NO. | : 10/098968 | |
| DATED | : September 11, 2012 | |
| INVENTOR(S) | : Stergis and McDonald | |

It is certified that error appears in the above-identified patent and that said Letters Patent is hereby corrected as shown below:

On the title page, item [56]; under Other Publications: "beclomethaone" should read "beclomethasone";

Column 2, line 20: "used" should read "use";

Column 4, line 32: after activity the second "in the" should be deleted;

Column 12, line 8: after prednisone "and" should read "or";

Column 12, line 46: after prednisone "and" should read "or".

Signed and Sealed this
Twenty-third Day of October, 2012

David J. Kappos
*Director of the United States Patent and Trademark Office*